(12) United States Patent
Lovhaug et al.

(10) Patent No.: US 8,182,790 B2
(45) Date of Patent: *May 22, 2012

(54) CONTRAST AGENTS

(75) Inventors: Dagfinn Lovhaug, Oslo (NO); Morten Eriksen, Oslo (NO); Hege B. Fjerdingstad, Oslo (NO); Andrew Healey, Oslo (NO)

(73) Assignee: GE Healthcare AS, Oslo (NO)

( * ) Notice: Subject to any disclaimer, the term of this patent is extended or adjusted under 35 U.S.C. 154(b) by 740 days.

This patent is subject to a terminal disclaimer.

(21) Appl. No.: 11/719,662

(22) PCT Filed: Nov. 21, 2005

(86) PCT No.: PCT/NO2005/000435

§ 371 (c)(1),
(2), (4) Date: Jan. 27, 2009

(87) PCT Pub. No.: WO2006/054904

PCT Pub. Date: May 26, 2006

(65) Prior Publication Data

US 2009/0208412 A1    Aug. 20, 2009

(30) Foreign Application Priority Data

Nov. 22, 2004    (NO) .................................. 20045081

(51) Int. Cl.
*A61K 49/00* (2006.01)

(52) U.S. Cl. ...... 424/9.1; 424/1.11; 424/1.65; 424/1.69; 424/9.4; 424/9.6

(58) Field of Classification Search ................ 424/1.11, 424/1.65, 1.69, 1.81, 1.85, 1.89, 9.1, 9.3, 424/9.4, 9.5, 9.6, 9.7, 9.8; 530/300, 311, 530/317, 318, 321, 330, 331, 333, 334, 338; 206/223, 569, 570

See application file for complete search history.

(56) References Cited

U.S. PATENT DOCUMENTS

| | | | |
|---|---|---|---|
| 5,942,637 A | 8/1999 | Boudjouk et al. | |
| 6,264,914 B1 * | 7/2001 | Klaveness et al. | 424/1.65 |
| 6,852,318 B1 | 2/2005 | Varner | |
| 7,351,790 B2 * | 4/2008 | Cuthbertson et al. | 530/317 |
| 7,431,914 B2 * | 10/2008 | Cuthbertson et al. | 424/1.69 |
| 7,488,468 B1 | 2/2009 | Miwa et al. | |
| 7,521,419 B2 * | 4/2009 | Cuthbertson et al. | 514/1.1 |
| 7,608,243 B2 * | 10/2009 | Cuthbertson et al. | 424/1.69 |
| 7,737,252 B2 | 6/2010 | Cuthbertson | |
| 7,763,234 B2 * | 7/2010 | Lovhaug | 424/1.69 |
| 7,897,142 B2 * | 3/2011 | Cuthbertson et al. | 424/9.6 |

FOREIGN PATENT DOCUMENTS

| | | |
|---|---|---|
| WO | WO 90/09195 | 8/1990 |
| WO | 01/77145 | 10/2001 |
| WO | 02/055111 | 7/2002 |
| WO | 03/006491 | 1/2003 |
| WO | WO 03/105886 | 12/2003 |
| WO | 2005/003166 | 1/2005 |
| WO | 2005/012335 | 2/2005 |
| WO | 2005/019247 | 3/2005 |
| WO | 2005/123767 | 12/2005 |

OTHER PUBLICATIONS

PCT/NO2005/000435 Int'l Search Report & Written Opinion dated Feb. 6, 2007.
Haubner, R. et.al., "Radiolabeled tracers for imaging of tumor angiogenesis and evaluation of anti-angiogenic therapies" Current Pharmaceutical Design, Bentham Science Publishers, Schiphol, NL, vol. 10, No. 13, May 2004 pp. 1439-1455.
Hagen Van, P.M., et.al. "Evaluation of a radiolabelled cyclic DTPA-RGD analogue for tumour imaging and radionuclide therapy" Int'l Journal of Cancer, New York, NY, vol. 90, No. 4, Aug. 2000 pp. 186-198.

\* cited by examiner

*Primary Examiner* — D L Jones

(57) ABSTRACT

A contrast agent of the general formula (I): $Z_1$-L-V-$Z_2$ (I) wherein at least one of Z1 and Z2 is present and are equal or different reporter moieties detectable in in vivo imaging of the human or animal body, V is a targeting moiety with binding affinity for areas of collagen formation, L is a covalent bond, a biomodifier or a linker moiety.

26 Claims, No Drawings

```
                        SEQUENCE LISTING

<160> NUMBER OF SEQ ID NOS: 3

<210> SEQ ID NO 1
<211> LENGTH: 10
<212> TYPE: PRT
<213> ORGANISM: Artificial
<220> FEATURE:
<223> OTHER INFORMATION: Synthesised Peptide
<220> FEATURE:
<221> NAME/KEY: THIOETHER
<222> LOCATION: (1)..(8)
<223> OTHER INFORMATION: Thioether bridge between residues 1 and 8
<220> FEATURE:
<221> NAME/KEY: DISULFIDE
<222> LOCATION: (2)..(6)
<223> OTHER INFORMATION: Disulfide bridge between residues 2 and 6

<400> SEQUENCE: 1

Lys Cys Arg Gly Asp Cys Phe Cys Gly Lys
1               5                   10

<210> SEQ ID NO 2
<211> LENGTH: 11
<212> TYPE: PRT
<213> ORGANISM: Artificial
<220> FEATURE:
<223> OTHER INFORMATION: Synthesised Peptide
<220> FEATURE:
<221> NAME/KEY: THIOETHER
<222> LOCATION: (1)..(9)
<223> OTHER INFORMATION: Thioether bridge between residues 1 and 9
<220> FEATURE:
<221> NAME/KEY: DISULFIDE
<222> LOCATION: (2)..(6)
<223> OTHER INFORMATION: Disulfide bridge between residues 2 and 6

<400> SEQUENCE: 2

Lys Lys Cys Arg Gly Asp Cys Phe Cys Gly Lys
1               5                   10

<210> SEQ ID NO 3
<211> LENGTH: 9
<212> TYPE: PRT
<213> ORGANISM: Artificial
<220> FEATURE:
<223> OTHER INFORMATION: Synthesised Peptide
<220> FEATURE:
<221> NAME/KEY: THIOETHER
<222> LOCATION: (1)..(8)
<223> OTHER INFORMATION: Thioether bridge between residues 1 and 8
<220> FEATURE:
<221> NAME/KEY: DISULFIDE
<222> LOCATION: (2)..(6)
<223> OTHER INFORMATION: Disulfide bridge between residues 2 and 6

<400> SEQUENCE: 3

Lys Cys Arg Gly Asp Cys Phe Cys Gly
1               5
```

CONTRAST AGENTS

This application is a filing under 35 U.S.C. 371 of international application number PCT/NO2005/000435, filed Nov. 21, 2005, which claims priority to application number 20045081 filed Nov. 22, 2004, in Norway the entire disclosure of which is hereby incorporated by reference.

FIELD OF INVENTION

The present invention relates to new contrast agents and their use in diagnostic imaging techniques. More specifically the invention relates to contrast agents comprising targeting vectors that bind to areas of collagen formation and extra-cellular matrix, ECM. Such contrast agents may be used for targeting of active fibrosis (collagen deposition) and the diagnosis of a number of disease conditions like for example heart failure, liver and lung fibrosis, retroperitoneal fibrosis, atherosclerosis, arthritis, cancer and skin disorders. Further such contrast agent can be used to show chronic cicatrizing inflammatory conditions, scar tissue and adherences, investigation of infarct size, show earlier infarcts and diagnosis of congestive heart failure.

BACKGROUND OF INVENTION

Collagens are the most abundant proteins in the animal kingdom. Twenty-five different types are currently known. The basic structural unit is a triple helix; in collagen I, the helix consists of three polypeptides, each containing 1050 amino acids. Collagen fibrils form by lateral interactions between the triple helices. Some collagens, notably collagen IV, form two-dimensional sheets.

The amino acid sequences of collagen molecules are highly repetitive, and this regularity is reflected in the structure of collagen fibrils. The amino acid sequence of collagen I contains about 20 copies of an 18-amino acid motif in which every third amino acid is a glycine.

The various collagens are produced by fibroblasts and some epithelial cells. The original transcript is a pro-collagen polypeptide that contains signal sequences for export from the cell and also a pro-peptide that prevents association to form triple helices. About 50% of proline residues and 15-20% of the lysines in pro-collagen chains are subject to intracellular processing to form hydroxyproline and hydroxy-lysine. These modifications are essential for the mechanical properties of collagen. Outside the cell, the pro-peptides are cleaved off, starting the process of self-assembly.

Collagens are essential components of structures such as bones and tendons and also of extra-cellular matrix in general. For instance, collagen IV forms the basic network of the basement membranes to which epithelial and endothelial cells attach. Part of the diversity of collagens is explained by the different types of collagen, but there is also a large variety of collagen-associated molecules. Collagen fibres are usually associated with proteoglycans. These proteins, consisting of a core polypeptide and one or more glucosaminoglycan side chains, are also a very diverse class. In the basement membrane, laminin and entactin (nidogen) are important components. The fibulins are a class of proteins with binding sites for several basement membrane proteins. Undulin is a fibre-forming protein that is found in association with collagen in low amounts in normal liver, and in high amounts in fibrotic liver.

Collagen and other proteins in connective tissue contain the Arg-Gly-Asp amino acid sequence, which confers binding to the integrin class of cell adhesion molecules. Other amino acid sequences may also constitute the core binding motif, and other parts of the ligand contribute to affinity as well as specificity. The β1 integrins are important in collagen binding. Other collagen-binding proteins include the discoidin domain receptors, which respond to collagen by activating a tyrosine kinase.

Collagen fibres are laterally flexible, but neither elastic nor compressible. Elastic properties of connective tissue are contributed by the protein elastin and its associated proteins oxytalan and elaunin. Fibrillins 1 and 2 are other proteins that form elastic fibres in association with elastin and another structural component, microfibril-associated glycoprotein. Abnormal elastic fibres are found in areas of hepatic fibrosis.

Deposition of collagen is a common process in healing of injury, leading to the formation of the familiar "scar tissue". Collagen deposition is a process that decreases the functionality of the tissue. This is obvious where elasticity of the tissue is important, a salient example being the scar tissue that forms during healing of a myocardial infarction. In the liver, the effects of rigid fibres are less obvious. Part of the process of liver fibrosis is deposition of extra-cellular matrix material in the space between the hepatocytes and the fenestrated endothelium of hepatic sinusoids, coincident with the transformation of sinusoids into capillaries that have an ordinary basement membrane. This transformation diminishes the functionality of the liver by impeding the transfer of solutes between the blood and the hepatocytes.

Hepatic fibrosis starts with injury that causes damage or death of liver cells. The injury initiates an inflammatory response. Release of cytokines, chemotactic factors and fragments of ECM matrix proteins (collagen and fibronectin) cause activation of liver cells and recruitment of inflammatory cells, such as granulocytes. Inflammation, including oxidative stress, is the common factor of most causes of hepatic fibrosis. An important event is the activation of stellate cells (aka fat-storing cells or Ito cells). The best-known function of these cells in the normal liver is to store vitamin A. On activation, they lose their vitamin A and differentiate into myofibroblasts. These cells are the collagen-producing cells.

Causative agents of liver fibrosis are numerous: alcohol, hepatitis viruses, cholangitis, hemachromatosis, Wilson's disease and schizostomiasis. In experimental animals (usually rats), fibrosis may be induced by carbon tetrachloride or thioacetamide. Most of these agents produce distinct patterns of liver injury, including collagen deposition. The role of the inflammatory response is variable; in some conditions, for instance hemochromatosis, oxidative stress is important.

If the injury is limited in extent and in time, the resulting fibrosis is reversible. In the liver, prolonged stress may lead to cirrhosis, characterised by general damage, formation of regeneration nodules, and fibrosis that distorts liver architecture. In rats, collagen Type I have a half-life of 30 days and Type III has a half-life of 15 days. When cirrhosis is induced by carbon tetrachloride, the half-lives of both collagens are reduced by 50%. Amounts of collagen reach levels 5-10 times higher than normal values (but never above 30-35 mg/g).

The point of diagnosis and treatment of hepatic fibrosis is the prevention of irreversible liver damage and consequent reduced function. Increased amount and altered patterns of collagen deposition indicate liver fibrosis. A positive biopsy is considered the definitive answer. Biopsies are invasive procedures with a frequency of significant complications of 1-5%. Single unguided biopsies will miss cirrhosis in 10-30% of cases. Correct diagnosis may increase to 100% if three specimens are examined. As the incidence of complications increases with the number of biopsies taken, it appears that triple biopsies may increase the incidence of complications to the order of 10%. Furthermore, evaluation of biopsies is far from straight-forward.

Within any stage of liver disease, there is up to a four-fold variation in the area of fibrosis; furthermore, there is a substantial overlap in the area of fibrosis between different stages. Consequently, the amount of collagen, as calculated by computer-aided image analysis, is of little value in deciding the stage of fibrosis. Experienced observers using standardised scoring schemes do provide reliable information on staging. In fact, these systems work so well that there is little incentive to look beyond collagen for additional histological markers. However, the ECM matrix protein tenascin is deposited in early lesions and is often absent from mature scar tissue, while vitronectin is a marker of mature fibrous tissue.

Serological markers for liver fibrosis that are used up to now may be divided in two groups: Markers for alterations in hepatic function (platelet counts, liver trans-aminases) and markers for ECM turnover. The latter may include markers of collagen deposition (e.g., circulating collagen pro-peptides) and/or collagen degradation (e.g., circulating fragments of collagen IV). A combination of carefully selected markers may give much more precise results than single markers, but there is no universal agreement on this issue.

There is clearly a need for a reliable test that can diagnose fibrosis in the early stages, before irreversible damage occurs. A very desirable feature of future tests is the ability to quantify changes in the ECM.

As explained above, excessive deposition of collagen reduces the elasticity of the tissue. This also includes the scar tissue that forms during healing of a myocardial infarction. Following injury to the heart or persistent increase in stress in the cardiac wall, the heart attempts to compensate by remodelling. This process implies progressive alterations in the size and shape of the ventricular chambers, coupled with changes in the composition of the myocardium. Typical responses include enlargement of surviving myocytes and changes in the types, cross-linking and concentration of collagen. It appears that initially, the extra-cellular matrix is partially degraded concurrent with hypertrophy of cardiac myocytes. Subsequently, there is a chronic compensatory phase as the collagen concentration returns to normal. But if the heart is unable to compensate, remodelling results in marked ventricular dilatation in spite of prominent fibrosis. The end stage of cardiac failure is characterised by further remodelling of the extra-cellular matrix concurrent with disorganisation of myofibrils and loss of myocytes. Collagen continues to accumulate, but collagen fibrils are laid down in an irregular manner.

Fibrosis is a component of more than 200 lung diseases. Repeated injury or sustained stress e.g., inflammation and/or inhaled particles, are common components of the etiology, along with genetic factors that turn the balance in the direction of deposition of connective tissue. One example is deficiency of $\alpha_1$-proteinase inhibitor, a protein whose activity may also be reduced as a consequence of smoking. Its main function is to inhibit neutrophil elastase. As in fibrosis of other organs, imbalance between synthesis and degradation may initiate repair processes that actually injure function. As in fibrosis of the heart or the liver, myofibroblasts figure prominently in the pathology. They are originally recruited as fibroblasts that subsequently differentiate. It appears that the "repair process" may continue in the absence of perceptible inflammation, resulting in progressive loss of function.

DESCRIPTION OF RELEVANT ART

WO 89/10758 describes compounds for binding to the surface membrane of bioparticles. These compounds comprise a bio-affecting substance and at least one hydrocarbon substituent is selected so that the compound is sufficiently non-polar to impart lipid binding capability to the compound wherein the bio-affecting substance can be a cyanine dye.

WO 93/11120 describes compounds that bind to lipid containing biocompatible particles such as cells and viruses. These compounds are selected so that the compounds are sufficiently non-polar to impart lipid binding capability to the compound.

SUMMARY OF INVENTION

The present invention provides new contrast agents useful in diagnosis and monitoring of treatment of diseases related to the excessive formation of collagen. Diseases and indications associated with excessive collagen deposition are e.g. heart failure, lung and liver fibrosis, atherosclerosis, arthritis and skin disorders.

Thus, the present invention provides contrast agents useful in the diagnosis of heart failure and other diseases involving excessive collagen deposition such as those mentioned above, comprising a targeting moiety incorporating one or more imageable moiety. The imageable moiety/moieties can be any imageable moiety which when administered to a subject can generate an image of at least a part of said subject to which said contrast agent has distributed, e.g. by radio imaging, Single Photon Emission Computed Tomography (SPECT), Positron Emission Tomography (PET), Magnetic Resonance Imaging (MRI), X-ray, optical imaging (OI), ultrasound (US), electrical impedance or magnetometric imaging modalities.

The present invention further provides methods of imaging of said diseases and also methods of monitoring of progression of treatment for such diseases. The invention also provides novel pharmaceutical compositions and precursors for the preparation of diagnostic contrast agents. Kits of contrast agents, in particular kits for the preparation of radiopharmaceutical contrast agents are provided.

The contrast agents of the invention are described by the general formula (I):

$$Z_1\text{-L-V-}Z_2 \qquad (I)$$

that will be further described hereinafter.

DETAILED DESCRIPTION OF THE INVENTION

Viewed from one aspect the invention provides contrast agents of formula (I) as defined in the claims. In the contrast agent of the general formula (I):

$$Z_1\text{-L-V-}Z_2 \qquad (I)$$

at least one of $Z_1$ and $Z_2$ is present and are equal or different reporter moieties detectable in in vivo imaging of the human or animal body, V is a targeting moiety with binding affinity for areas of collagen formation, L is a covalent bond, a biomodifier or a linker moiety.

Z is hereinafter used to denote either one of or both $Z_1$ and $Z_2$. Z can be any imageable moiety.

For contrast agents useful in diagnosis and particularly in in vivo diagnosis the moieties Z comprise the imageable moiety or moieties. When the imageable moiety itself cannot be bound directly to V or L (when present), e.g. when the imageable moiety is a metal particle or a metal ion hereinafter denoted M, then Z comprises a moiety $Y_1M$ where $Y_1$ is a moiety capable of binding to V or L (when present) and at the same time carrying M. By carrying is meant any form of association between the moiety $Y_1$ and M such as a chemical bond, e.g. covalent bond or electrovalent or ionic bonds or by absorption or any other type of association.

Where M is a metal particle or metal ion then $Y_1$ represents a chelating agent.

The nature of Z and/or $Y_1M$ will depend of the imaging modality utilised in the diagnosis. Z and/or $Y_1M$ must be capable of detection either directly or indirectly in an in vivo diagnostic imaging procedure, e.g. moieties which emit or may be caused to emit detectable radiation (e.g. by radioactive decay, fluorescence excitation, spin resonance excitation, etc.), moieties which affect local electromagnetic fields (e.g. paramagnetic, superparamagnetic, ferrimagnetic or ferromagnetic species), moieties which absorb or scatter radiation energy (e.g. chromophores, particles (including gas or liquid containing vesicles), heavy elements and compounds thereof, etc.), and moieties which generate a detectable substance (e.g. gas microbubble generators).

Chelating agents of formula (II) and (III) hereinafter are particularly preferred.

A wide range of suitable imageable moieties are known from e.g. WO 98/18496, the content of which is incorporated by reference.

Imaging modalities and imageable moieties Z and M are described in more detail hereinafter:

In a first embodiment, the moiety Z in the compound of formula (I) comprises a moiety $Y_1$ carrying one or more imageable moieties M useful in the Radio and SPECT imaging modality. Preferably M is a gamma emitter with low or no alpha- and beta-emission and with a half-life of more than one hour. Preferred groups M are the radionuclides $^{67}Ga$, $^{111}In$, $^{123}I$, $^{125}I$, $^{131}I$, $^{81m}Kr$, $^{99}Mo$, $^{99m}Tc$, $^{201}Tl$ and $^{133}Xe$. Most preferred is $^{99m}Tc$.

M can further be represented by the following isotopes or isotope pairs for use both in imaging and therapy without having to change the radiolabelling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

When M denotes a metallic radionuclide then $Y_1$ denotes a chelating agent suitable for forming a stable chelate with M. Such chelating agents are well known from the state of art and typical examples of such chelating agents are described in Table I of WO 01/77145.

Particularly preferred are chelating agents $Y_1$ of formula (II):

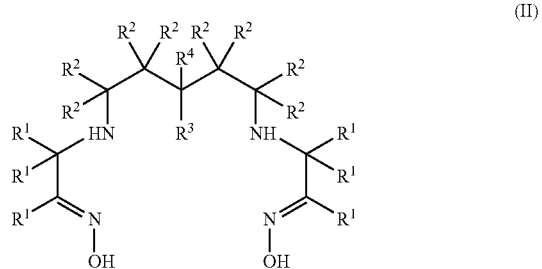

wherein each $R^1$, $R^2$, $R^3$ and $R^4$ independently represent H, $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents $Y_1$ of formula (II) where $R^1$, $R^2$ and $R^3$ are hydrogen or methyl groups and $R^4$ is an alkylamine group, most specifically a compound of formula (III), hereinafter denoted cPN216.

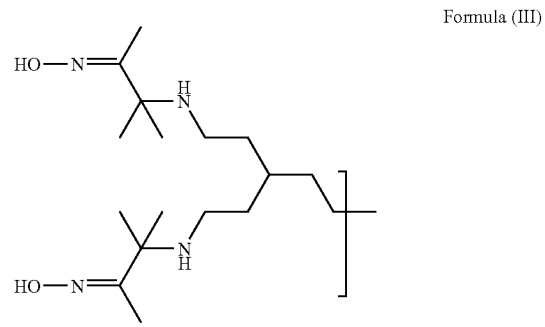

Most preferred for Z are the chelate of cPN216 with $^{99m}Tc$.

Synthesis of chelating agents of formula (II) and (III) are described in WO 03/006070.

Z groups of non-metal radionuclides such as $^{123}I$, $^{125}I$ and $^{131}I$ may be covalently linked to the moieties V and L (when present) by a substitution or addition reaction well known from the state of art.

In a second embodiment, the compound of formula (I) comprises a moiety Z useful in the PET imaging modality. Z then denotes a radioemitter with positron-emitting properties. Preferred groups Z are the radionuclides $^{11}C$, $^{18}F$, $^{68}Ga$, $^{13}N$, $^{15}O$ and $^{82}Rb$. $^{18}F$ is specifically preferred. The metallic radioemitters $^{82}Rb$ and $^{68}Ga$ chelated with a chelating agent $Y_1$ are also preferred.

Thiol coupling chemistry, $^{18}F$-synthons and labelled peptides prepared using the thiol coupling chemistry are described in WO 03/080544, the content of which is incorporated herein by reference.

Description of peptides labelled by use of thiol coupling chemistry can be found in WO2005/01235, the content of which is incorporated herein by reference.

In another preferred embodiment $Y_1$ denotes the DOTA chelating agent and M is $^{68}Ga$ which can be readily introduced into the chelating agent using microwave chemistry.

Z groups of non-metal radionuclides such as $^{18}F$ may be covalently linked to the moieties V and L (when present) by a substitution or addition reactions that are well known from the state of art and also described e.g. in WO 03/080544 which is hereby incorporated by reference.

In a third embodiment, the moiety Z of the compound of formula (I) comprises a moiety $Y_1$ carrying one or more imageable moieties M useful in the MR (Magnetic Resonance) imaging modality. M here denotes a paramagnetic metal ion such those mentioned in U.S. Pat. No. 4,647,447. The paramagnetic metal ions $Gd^{3+}$, $Dy^{3+}$, $Fe^{3+}$ and $Mn^{2+}$ are particularly preferred. $Y_1$ denotes a chelating agent, in particular a chelating agent such as acyclic or cyclic polyaminocarboxylates (e.g. DTPA, DTPA-BMA, DOTA and DO3A) as described e.g. in U.S. Pat. No. 4,647,447 and WO 86/02841.

In MR imaging M may also denote metal oxides such as superparamagnetic, ferrimagnetic or ferromagnetic species which are absorbed by Z, e.g. such that Z function as a coating to the metal oxide. Metal oxides for use as MR contrast agents are described e.g. in U.S. Pat. No. 6,230,777 which is hereby incorporated by reference.

In a fourth embodiment the moiety Z of the compound of formula (I) comprises a moiety $Y_1$ carrying one or more imageable moieties M useful in the X-ray imaging modality. M here denotes a heavy metal such as W, Au and Bi in the form of oxides which may be absorbed to Z or in the form of their metallic entities (oxidation state 0). Z may also represent iodinated aryl derivatives particularly well known as iodinated X-ray contrast agents, e.g. those known under their trade names Iopamidol™ and Omnipaque™. These agents can be linked via their amide or amine functions to the moieties V or L (where present) of formula (I).

In a further embodiment the compound of formula (I) comprises Z moieties in the form of gas filled microvesicles. Such ultrasound imaging agents can be utilised in the imaging of receptors e.g. when they are functionalised for binding to a peptide as described in the state of art e.g. in WO98/18500.

In a sixth embodiment of the present invention the moiety Z of formula (I) may be any moiety capable of detection either directly or indirectly in an optical imaging procedure. The detectable moiety can be a light scatterer (e.g. a coloured or uncoloured particle), a light absorber or a light emitter. More preferably Z is represented by a dye such as a chromophore or a fluorescent compound. The moiety Z can be any dye that interacts with light in the electromagnetic spectrum with wavelengths from the ultraviolet light to the near-infrared. In a preferred version Z has fluorescent properties.

Preferred organic dye moieties include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Preferred examples of optical imaging moieties are the cyanine dye (CyDye™). Cyanine dyes are compounds defined by a polyene chain containing an odd number of carbon atoms linked by alternating single and multiple, preferably double, carbon-carbon bonds, terminated at either end by an amino group, one of which is quaternised. The cyanine and analogues aryl-linker-aryl chromophores optionally carry pendant or fused ring substituents. General description of cyanine dyes and synthesis thereof are described in U.S. Pat. No. 6,048,982, U.S. Pat. No. 5,268,486 and EP patent no. 1 037 947 which are hereby incorporated by reference. The cyanine dyes are particularly useful due to the wide range of spectral properties and structural variations available. A range of cyanine dyes are well known and tested, they have low toxicity, and are commercially available (GE Healthcare, formerly Amersham Biosciences). The cyanine dyes are a single family of highly intense dyes with good aqueous solubility. They are pH insensitive between pH 3-10, exhibit low non-specific binding, and are more photostable than fluorescein.

Cyanine dyes is preferably selected from the groups consisting of carbacyanines, oxacyanines, thiacyanines and azacyanines shown below by general formulas.

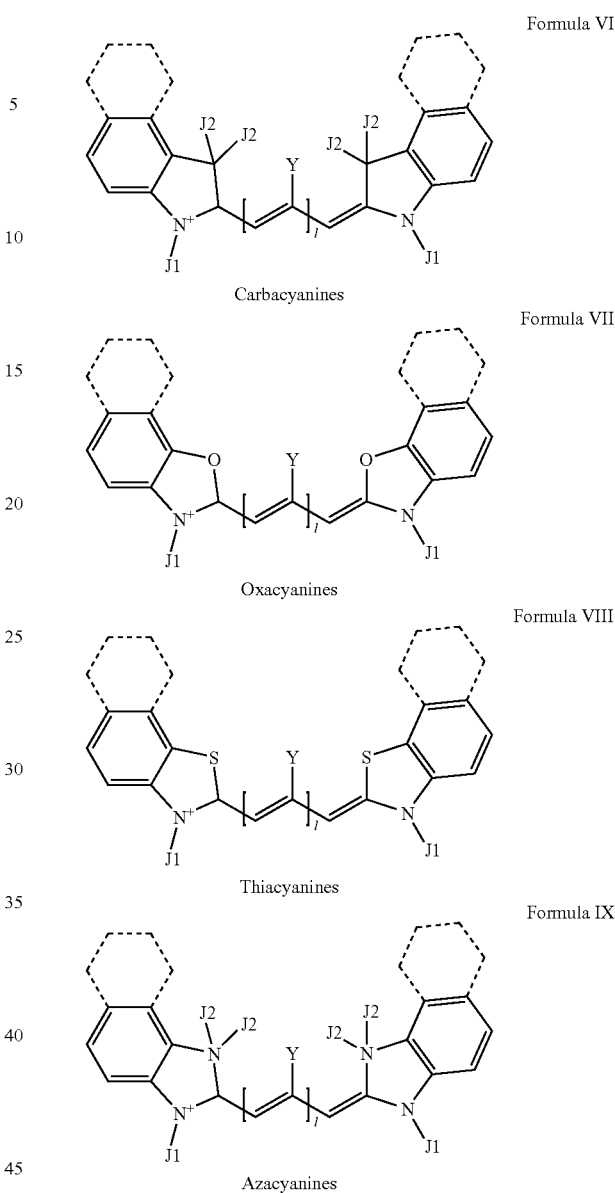

In these structures the J1-groups are the same or different and are substituted or unsubstituted alkyl groups, preferably C1 to C6 alkyls, and may comprise an ether or an —N—CO—N— group The alkyl groups are optionally substituted with carboxy, sulphonic acid, amine, ammonium or ester groups. The J1-groups may form bridges with any of the carbon-atoms of the polyene chains, e.g. by a —N—CO—N— group or an ether-group. The J2-groups are also the same or different and are substituted or unsubstituted alkyl groups. The alkyl groups are optionally substituted with carboxy or sulphonic acid groups, but preferably the J2-groups are lower alkyl groups, such as C1 to C6 alkyls, and most preferably methyl groups. Optional aromatic groups are indicated by dotted lines, to cover both structures comprising condensed benzo rings and condensed naphtho rings. The rings are substituted or unsubstituted. The rings may be substituted with sulphonic acid groups, carboxylic groups, hydroxyl groups, alkyl(sulphoalkyl)amino groups, bis(sulphoalkyl)amino groups, sulphoalkoxy groups, sulphoalkylsulphonyl group, alkyl or substituted alkyl or sulphoalkylamino groups. The alkyl-groups are preferably lower alkyls with e.g. 1 to 6 carbon atoms. Y is selected from hydrogen, a halide group, amine group or an sulphonyl, and is preferably hydrogen. The polyene chain of the cyanine dye may also contain one or more cyclic chemical group that forms bridges between two or more of the carbon atoms of the polyene chain, e.g. by including a —CO— group between two of the carbon atoms of the chain, as in the squaraine dyes, or by including an alkyl bridge. These bridges might serve to increase the chemical or photostability of the dye.

In the formulas VI to IX, I is a positive integer 1, 2, 3 or 4 giving trimethinecyanines, having a carbon-bridge of three carbon atoms, pentamethine, heptamethine or nonamethine cyanine dyes. Preferably, the cyanine dye is a dye with carbon-bridges of 3, 5 or 7 carbon atoms, respectively.

J1 and J2 are potential linking sites for the linking of the dye to the targeting moiety V, optionally via a linker moiety L, with J1 being preferred. In a preferred aspect one J1 is linked to the targeting moiety V, while the other R1 group is a optionally substituted C1 to C6 alkyl group.

Further descriptions of moieties suitable in optical imaging procedures are found in WO 2005/003166, the content of which is hereby incorporated by reference.

The moiety V of the compound of formula (I) comprises the amino acid sequence $X_3$-G-D having affinity for areas of collagen formation. The compound preferably comprises further amino acids, and optional further moieties, wherein the $X_3$-G-D sequence is the binding seat of the peptidic vector which function as a vector binding to an area of collagen formation.

The compound of formula (I) of the invention can be constrained for example by formation of one or more cyclicising bridges in the peptidic vector part. A monocyclic peptide compound can be obtained by formation of a disulfide bond or a thioether bond between the amino acids. The compounds of formula (I) preferably comprise two cyclicising bridges between different amino acids of the compounds. The term "cyclicising bridges" refers to any combination of amino acids or with amino acids and the —$(CH_2)_n$— or the —$(CH_2)_n$—$C_6H_4$— groups with functional groups which allows for the introduction of a bridge. n represents a positive integer from 1 to 10. Preferred examples are disulphides, disulphide mimetics such as the —$(CH_2)_4$— carba bridge, thioacetal, thioether bridges (cystathione or lanthionine) and bridges containing esters and ethers. Preferably, one bridge forms a disulphide bond and a second bridge comprises a thioether (sulphide) bond.

In a further embodiment the vector V of formula (I) is represented by the formula (VI)

$R_a$—C(=O)—$X_1$—$X_2$—$X_3$-G-D-$X_4$—$X_5$—$X_6$      (VI)

and comprises two cyclicising bridges,
wherein,
$X_1$ represents a covalent bond or 1, 2, 3, 4 or 5 amino acid residues, wherein one of the amino acid residues optionally is functionalised with a linker moiety L and preferably said amino acid residues possesses a functional side-chain such as an acid or amine group preferably selected from aspartic or glutamic acid, lysine, ornithine, diaminobutyric acid or diaminopropionic acid;

$X_2$ and $X_4$ represent independently amino acids residues capable of forming a cyclicising bridge, such as cysteine or homocysteine residues forming disulphide or thioether bonds, or other amino acid residues capable of forming a cyclicising bridge such as aspartic acid and lysine, preferably $X_2$ and $X_4$ represent residues of cysteine or homocysteine;

$X_3$ represents arginine, N-methylarginine or an arginine mimetic;

$X_5$ represents a hydrophobic amino acid or derivatives thereof, and preferably represents a tyrosine, a phenylalanine, a 3-iodo-tyrosine or a naphthylalanine residue, and more preferably a phenylalanine or a 3-iodo-tyrosine residue;

$X_6$ represents an amino acid residue capable of forming a cyclicising bridge, preferably a thiol-containing amino-acid residue, preferably a cysteine or a homocysteine residue; and $R_a$ represents the moieties —$(CH_2)_n$— or —$(CH_2)_n$—$C_6H_4$— capable of forming a bridge to either of $X_2$, $X_4$ or $X_6$; and n represents a positive integer from 1 to 10.

In one aspect of the invention the moiety L of formula (I) represents a homogeneous biomodifier moiety preferably based on a monodisperse PEG building block comprising 1 to 10 units of said building block, said biomodifier having the function of modifying the pharmacokinetics and blood clearance rates of the said agents. Additionally, L may also represent 1 to 10 amino acid residues preferably glycine, lysine, aspartic acid or serine. In a preferred embodiment, L represents a biomodifier unit comprising a monodisperse PEG-like structure, the 17-amino-5-oxo-6-aza-3,9,12,15-tetraoxaheptadecanoic acid of formula (V),

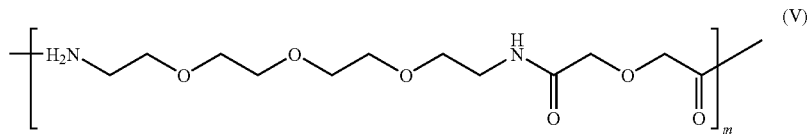

wherein m equals an integer from 1 to 10 and where the C-terminal unit is an amide moiety.

As noted above, the biomodifier, L, modifies the pharmacokinetics and blood clearance rates of the compounds. The biomodifier effects decreased uptake of the compounds in the tissues i.e. in muscle, liver etc. thus giving a better diagnostic image as a result of less background interference. The secretion is mainly through the kidneys and this adds a further advantage of the biomodifier.

L can further represent a moiety preferentially derived from glutaric and/or succinic acid and/or a polyethyleneglycol based unit and/or a unit of formula (V) as illustrated above.

Other representative L elements include structural-type polysaccharides, storage-type polysaccharides, polyamino acids and methyl and ethyl esters thereof, and polypeptides, oligosaccharides and oligonucleotides, which may or may not contain enzyme cleavage sites.

The peptides of the present invention can be synthesised using all known methods of chemical synthesis but particularly useful is the solid-phase methodology of Merrifield employing an automated peptide synthesiser (J. Am. Chem. Soc., 85: 2149 (1964)). Standard procedures for the synthesis strategy are described in E. Atherton & R. C. Sheppard, "Solid phase peptide synthesis: a practical approach, 1989, IRL Press, Oxford.

A synthesis resin with an acid-labile linker group, to which the desired protected C-terminal amino acid residue is attached by amide bond formation, is used. For example, a so-called Rink amide AM resin with a (dimethoxyphenyl-aminomethyl)-phenoxy-derived linker may be applied (Rink, H. (1987), Tetrahedron Lett. 30, p. 3787). Acidolytic clevage of the peptide from this resin will yield a peptide amide. Alternatively, a O-Bis-(aminoethyl)ethylene glycol trityl resin (K. Barlos et al (1988), Liebigs Ann. Chem., p. 1079) can be used that upon acidolytic cleavage yields a peptide with a primary amine handle.

The peptidyl resins are assembled in a C-terminal to N-terminal direction. The $N^\square$-amino-protecting group of the C-terminal amino acid is first removed and the second amino acid in the sequence is coupled using a suitable condensation reagents. $N^\square$-amino-deprotection and coupling cycles are then repeated in alternating steps until the desired sequences is assembled.

Generally, all reactive groups present are protected during peptide synthesis. A wide range of protecting groups for amino acids is known (see, e.g., Greene, T. W. & Wuts, P. G. M. (1991) Protective groups in organic synthesis, John Wiley & Sons, New York). An orthogonal protecting group strategy (Barany, G. et al (1977), J. Am. Chem. Soc, 99, p. 7363) can be used. Thus for example, combining different amine protecting groups such as the piperidine-labile 9-fluorenyl-methoxy-carbonyl (Fmoc) group with the super acid-labile 4-methyltrityl (Mtt) group, the hydrazine-labile 2-acetyldimedone (Dde) group and the acid-labile tert-butyloxycarbonyl (Boc) group it is possible to selectively introduce different moieties at different amine sites. Furthermore, by combining the acid-labile trityl (Trt) protecting group for the Cys side chain with tert-butyl protection of other Cys residues (labile under acidic oxidative conditions e.g. TFA-2% dimethylsulfoxide) selective disulfide formation is achieved.

Completed peptidyl resins can be chloroacetylated at the N-terminus to introduce a thioether bridge between the N-terminus and a Cys residue.

The peptides are labelled with $^{99m}$Tc by treating a compound dissolved in distilled and oxygen-free buffered solution (pH about 9) and held under nitrogen atmosphere with Sn-MDP and Na$^{99m}$TcO$_4$ solution as known from the state of art.

The invention is further illustrated by the non-limiting examples 1 to 4. The examples describe the synthesis of compounds with two different Z and/or Y$_1$M moieties. Also described is the labelling of the compounds with $^{99m}$Tc.

The position of the various amino acids in the peptides is visualised by superscript numbering (e.g. Cys$^2$).

EXAMPLES

Example 1

Cys2-6; c[CH$_2$CO-Lys(N-(5-sulfo-naphthalen-2-yl)-Succ)-Cys-Arg-Gly-Asp-Cys-Phe-Cys]-GlutcPn216)-NH$_2$ (4) and its $^{99m}$Tc chelate (4a)

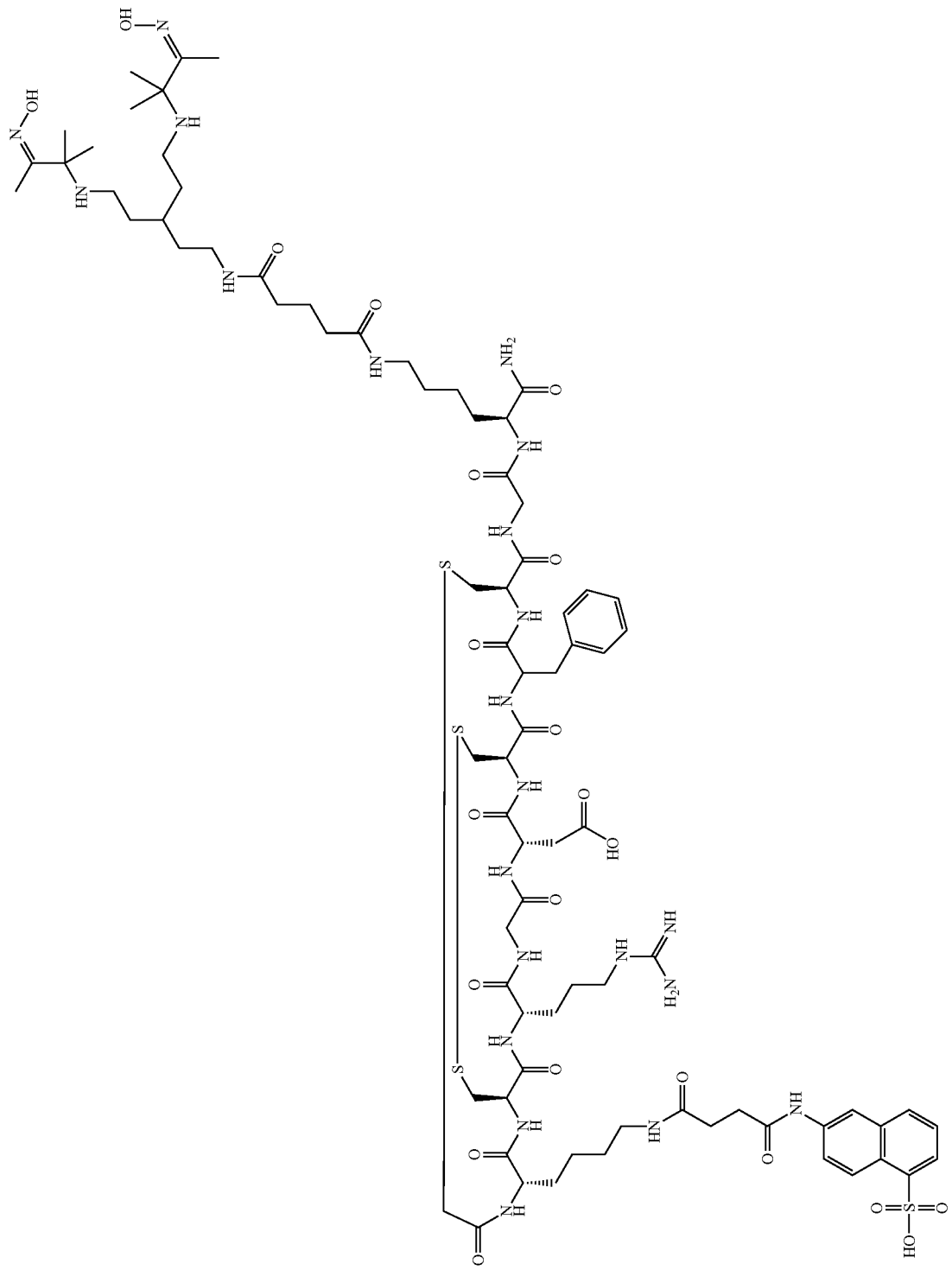

4a
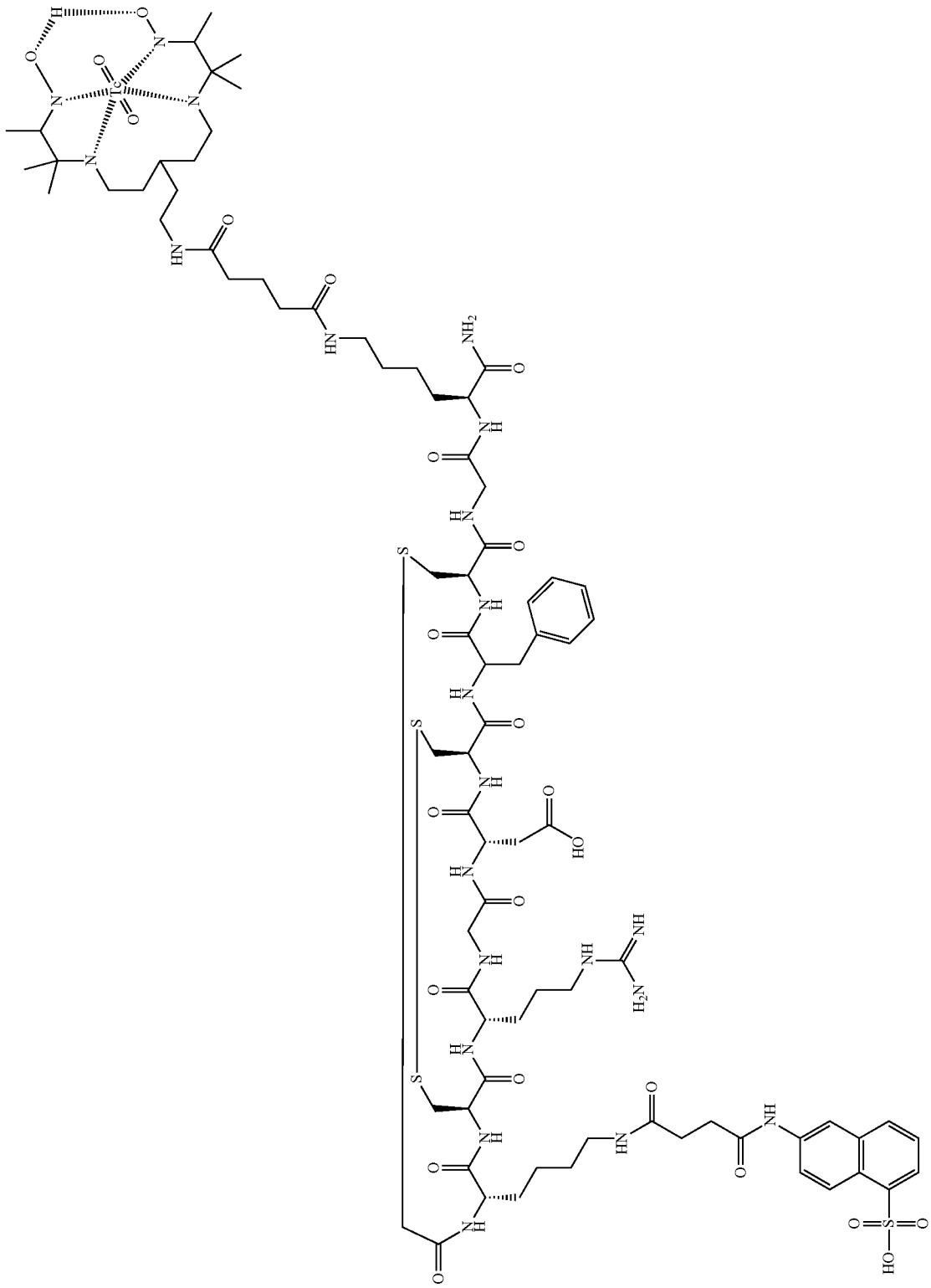
-continued

Solid-phase synthesis of ClCH$_2$CO-Lys-Cys(tBu)-Arg(Pmc)-Gly-Asp(tBu)-Cys(tBu)-Phe-Cys(Trt)-Gly-Lys(Boc)-Rink Amide MBHA resin 1

The peptidyl resin corresponding to the above sequence was assembled by standard solid-phase peptide chemistry (Barany, G; Kneib-Cordonier, N; Mullenm D. G. (1987) *Int. J. Peptide Protein Research* 30, 705-739) on a Rink Amide MBHA resin (0.73 mmol/g; from NovaBiochem). An Applied Biosystems (Perkin Elmer) model 433A peptide synthesizer was used. The residues (from the carboxyl terminus) were assembled on a 0.25 mmol scale using single couplings with a 4-fold molar excess of N$^\alpha$-Fmoc-protected amino acids (1 mmol cartridges) and 2-(1H-benzotriazol-1-yl)-1,1,3,3-tetramethyluronium-hexafluorophosphate (HBTU)/1-hydroxy-benzotriazole (HOBt)/diisopropylethyl-amine (DIEA) in N-methylpyrrolidone (NMP) using 2.5 hours coupling cycles. Fmoc-deprotection was achieved with conductivity monitoring using 20% piperidine in NMP. The amino acid-side chain protecting groups used were 4-methyltrityl (Mtt) for Lys$^1$, tert-butyl (tBu) for Cys$^2$, Cys$^6$ and Asp, 2,2,5,7,8-pentamethylchroman-6-sulfonyl (Pmc) for Arg, trityl (Trt) for Cys$^8$, and tert-butyloxycarbonyl (Boc) for Lys$^{10}$.

The assembled peptidyl resin was then transferred to a manual nitrogen bubbler apparatus (Wellings, D. A., Atherton, E. (1997) in Methods in Enzymology (Fields, G. ed), 289, p. 53-54, Academic Press, New York). The N-terminus was Fmoc-deprotected and then chloroacetylated in dimethylformamide (DMF), using a 10-fold molar excess of the symmetric anhydride formed by reacting chloro-acetic acid (20 eq) with N,N'-diisopropylcarbodiimide (DIC) (10 eq) in dichloromethane (DCM). The Mtt-protecting group at N$^\epsilon$-Lys$^1$ was selectively removed by treating the peptidyl resin with DCM containing 5% triisopropylsilane (TIS) and 1% trifluoroacetic acid (TFA) for 5×2 minutes or until the filtrate became colorless. The completed peptidyl resin ClCH$_2$CO-Lys-Cys(tBu)-Arg(Pmc)-Gly-Asp(tBu)-Cys(tBu)-Phe-Cys(Trt)-Gly-Lys(Boc)-Rink Amide MBHA resin 1 was neutralized with 5% DIEA in DMF and finally washed with DMF and DCM and dried in vacuo.

Synthesis of Cys2-6; c[CH$_2$CO-Lys(N-(5-sulfo-naphthalen-2-yl)-Succ)-Cys-Arg-Gly-Asp-Cys-Phe-Cys]-Gly-Lys-NH$_2$ 3

6-Amino-1-naphtalenesulfonic acid (Dahl's acid) (1 eq, 0.5 mmol,) was dissolved in DMF containing N-methylmorpholine (NMM) (2 eq), and succinic anhydride (10 eq) was then added. After over night reaction the solvent was removed under reduced pressure and the product was purified by preparative RP-HPLC (Reversed Phase HPLC). The column (Phenomenex Luna C18 10μ, 22×250 mm) was eluted at 10 ml/min with a gradient of 5 to 15% acetonitrile (ACN) in 0.1% aq TFA over 40 min. The desired peak fractions collected from six consecutive runs were pooled and lyophilized affording 146 mg of pure N-(-5-Sulfo-naphthalen-2-yl)-succinamic acid 2. Analytical RP-HPLC: $t_R$=16.7 min, (Phenomenex Luna 5μ, 4.6×250 mm, 5-15% ACN in 0.1% aq TFA over 20 min at 1 ml/min, λ=214 nm). Electrospray MS: [M+H]$^+$ of product expected at 324.0 m/z, found at 324.0 m/z.

A solution of N-(-5-Sulfo-naphthalen-2-yl)-succinamic acid 2 (5 eq) and N-[(dimethylamino)-1H-1,2,3-triazolo-[4,5-b]pyridin-1-ylmethylene]-N-methylmethanaminium hexafluorophosphate N-oxide (HATU) (5 eq) in DMF containing NMM (15 eq) was added to the peptidyl resin 1. The reaction was let proceed over night in a manual nitrogen bubbler apparatus.

The peptide resin obtained was then treated with TFA containing 2.5% TIS and 2.5% water for 2 hours in order to cleavage the Cys$^{2,6}$ tBu-protected peptide from the resin while simultaneously removing all other side-chain protecting groups from the peptide. The resin residue was filtered off and washed with small quantities of neat TFA. The combined filtrate and washings were concentrated by rotary evaporation and then triturated with diethyl ether to obtain the crude peptide. The precipitate was isolated by centrifugation, washed with ether and then lyophilized from 50% ACN-0.1% aq TFA yielding 60 mg crude product.

The linear peptide was then cyclized, first by thioether bridge formation effected by stirring the peptide at 0.5 mg/ml in 50% ACN-water at pH 7.5 (adjusted by liquid ammonia) for 60 min at RT. The cyclized product was isolated by lyophilization. Secondly, the inner disulfide bridge was formed by simultaneous tBu-deprotection and disulfide formation in TFA-2% dimethylsulfoxide at 0.5 mg/ml over 60 min at RT. TFA was removed under reduced pressure and the peptide was isolated from ether and dried as described above, yielding 62 mg cyclic product. The crude peptide was purified by preparative RP-HPLC. The column (Phenomenex Luna C18 10μ, 50×250 mm) was eluted at 50 ml/min with a gradient of 15 to 20% ACN in 0.1% aq TFA over 60 min. The desired peak fractions were pooled and lyophilized affording 12 mg of pure product 3. Analytical RP-HPLC: $t_R$=12.9 min, (Phenomenex Luna 5μ, 4.6×250 mm, 15-25% ACN in 0.1% aq TFA over 20 min at 1 ml/min, λ=214 nm). Electrospray MS: [M+H]$^+$ of product expected at 1458.5 m/z, found at 1458.2 m/z.

Conjugation of cPN216-glutaryl to Peptide 3.

A solution of cPN216-glutaryl-tetrafluorothiophenyl ester (2 eq) in DMF was added to a solution of peptide 3 (1 eq, 0.008 mmol)) in DMF followed by NMM (6 eq). After stirring over night the reaction mixture was worked up by removing the solvent under reduced pressure followed by preparative RP-HPLC. The column (Phenomenex Luna C18 10μ, 22×250 mm) was eluted at 10 ml/min with a gradient of 13 to 20% ACN in 0.1% aq TFA over 60 min. The desired peak fractions collected were pooled and lyophilized affording 8 mg of pure compound 4. Analytical RP-HPLC: $t_R$=18.4 min, (Phenomenex Luna 5μ, 4.6×250 mm, 15-25% ACN in 0.1% aq TFA over 20 min at 1 ml/min, λ=214 nm). Electrospray MS: [M+H]$^{2+}$ of product expected at 949.4 m/z, found at 949.5 m/z.

$^{99m}$Tc-Labelling of Peptide 4

Peptide 4 (0.1 mg) was reconstituted in saline or methanol (0.1 ml) and transferred into a freeze dried Toolbox kit of excipients. The Toolbox kit, designed to provide generic radio labelling conditions for amine based chelates, contained stannous chloride dehydrate (16 μg), methylene diphosphonic acid (25 μg) sodium hydrogen carbonate (4500 μg), sodium carbonate (600 μg), sodium para-aminobenzoate (200 μg), Kit pH=9.2. Sodium Pertechnetate ($^{99m}$Tc) injection (2.1 GBq) in saline (3 ml) was then added, the kit was inverted a few times to dissolve the contents and then left to incubate at room temperature for 15-20 min. A sample was analyzed immediately by HPLC and ITLC and the $^{99m}$Tc-labelled peptide was administered to the trial subject between 1-3 hours after reconstitution of the kit.

Example 2

Cys2-6, c[CH$_2$CO-Lys(N-[5-sulfo-naphthalen-2-yl]-Succ-Lys(N-[5-sulfo-naphthalen-2-yl]-Succ)-Cys-Arg-Gly-Asp-Cys-Phe-Cys]-Gly-Lys(Glut-cPn216)-NH$_2$ (9) and its $^{99m}$Tc chelate (9a)

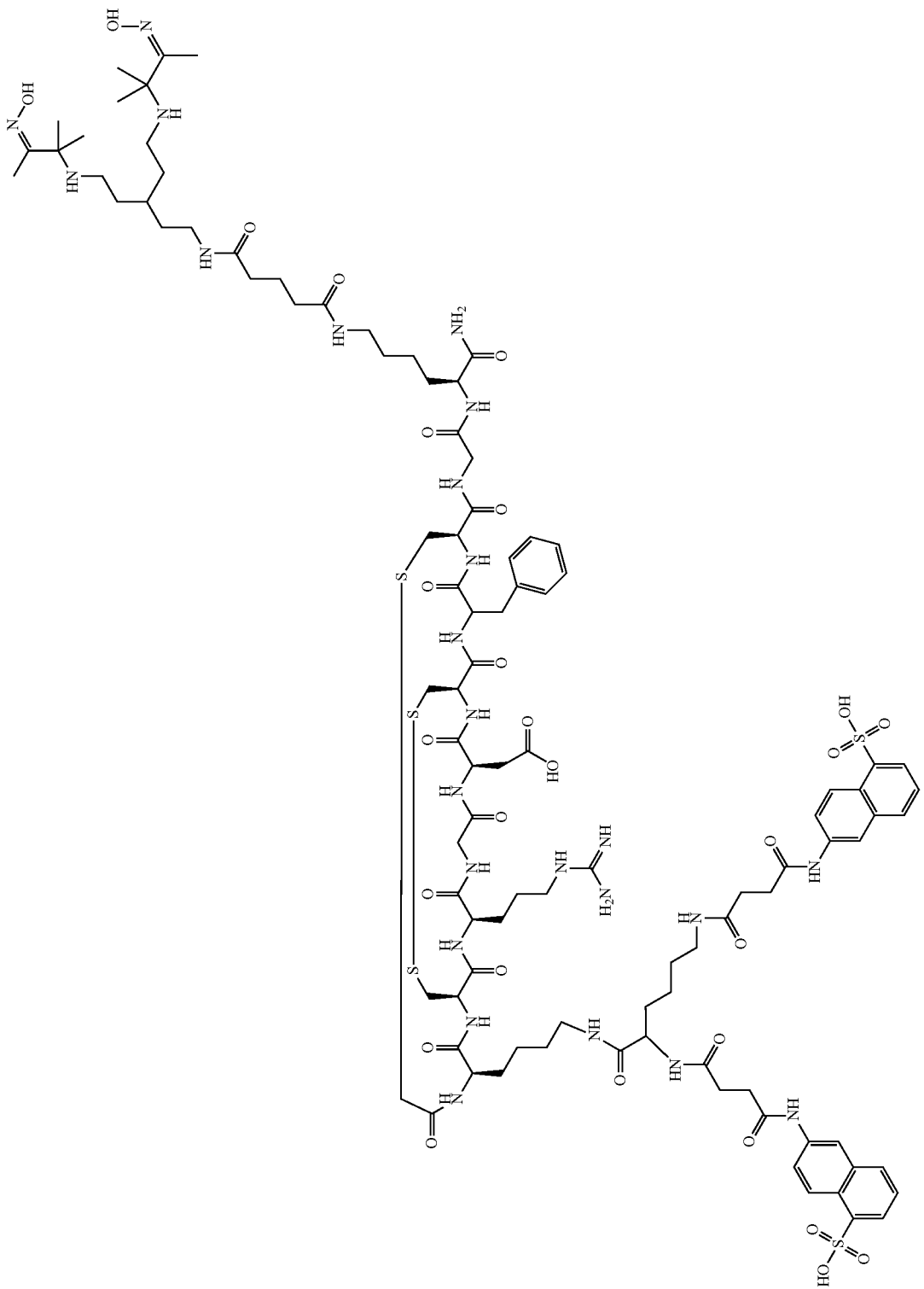

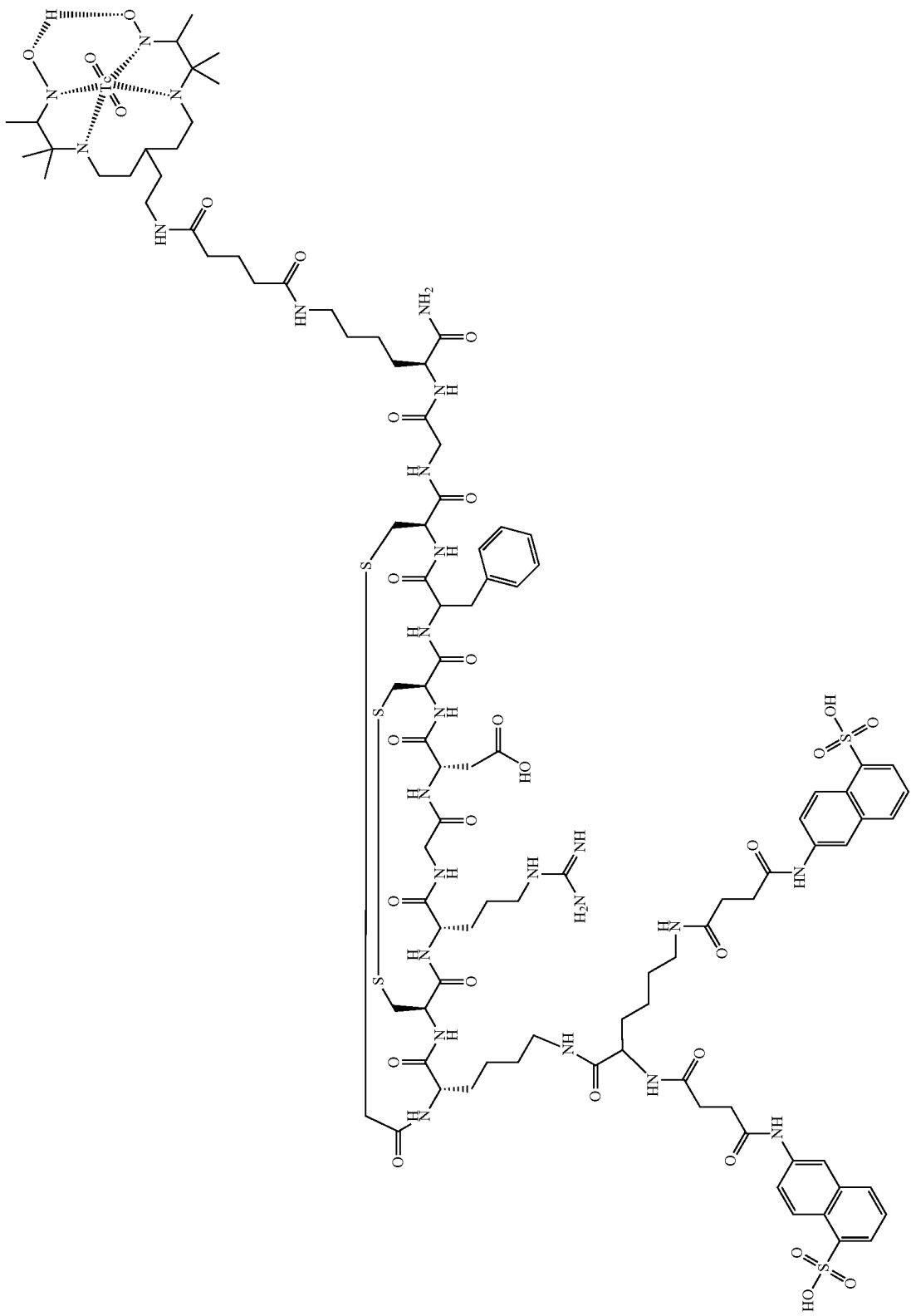

Synthesis of Cys2-6; c[CH$_2$CO-Lys-Cys-Arg-Gly-Asp-Cys-Phe-Cys]-Gly-Lys(Glut-cPn216)-NH$_2$ 7

The peptidyl resin 1 described in Example 1 above was N$^\epsilon$-Lys$^1$-protected by treatment with a solution of 2-acetyldimedone (Dde-OH) in DMF over 2 hours using a manual nitrogen bubbler apparatus. The partially protected peptide was cleaved from the resin upon treatment with TFA containing 2.5% TIS and 2.5% water for 2 hours. The reaction mixture was worked up and the peptide isolated from ether and lyophilized as described above in Example 1, yielding 70 mg of ClCH$_2$CO-Lys(Dde)-Cys(tBu)-Arg-Gly-Asp-Cys(tBu)-Phe-Cys-Gly-Lys-NH$_2$ 5.

The linear peptide 5 was cyclized by thioether bridge formation as described in Example 1 and the crude product (78 mg) was purified by preparative RP-HPLC. The column (Phenomenex Luna C18 10μ, 50×250 mm) was eluted at 50 ml/min with a gradient of 20 to 45% ACN in 0.1% aq TFA over 60 min. The desired peak fractions were pooled and lyophilized affording 26 mg of purified c[CH$_2$CO-Lys-Cys(tBu)-Arg-Gly-Asp-Cys(tBu)-Phe-Cys]-Gly-Lys-NH$_2$ 6. Analytical RP-HPLC: $t_R$=16.35 min, (Phenomenex Luna 5μ, 4.6×250 mm, 20-50% ACN in 0.1% aq TFA over 20 min at 1 ml/min, λ=214 nm). Electrospray MS: [M+H]$^{2+}$ of product expected at 716.8 m/z, found at 716.7 m/z.

The chelate cPN216-glutaryl-tetrafluorothiophenyl ester (2 eq) in DMF was then added to peptide 6 (1 eq, 0.009 mmol) followed by NMM (3 eq) and the mixture was stirred overnight. The Dde-group at N$^\epsilon$-Lys$^1$ was then removed by adding enough hydrazine to the reaction mixture to give a 2% solution. After 30 min the solvent was removed under reduced pressure and the product was isolated by precipitation and lyophilization as described above. Final tBu-deprotection and disulfide formation of the peptide was done as described in Example 1 yielding 18 mg of peptide 7.

Introduction of a Branched Dahl's Acid Moiety at the N$^\epsilon$-Lys$^1$-Position of Peptide 7

A solution of N—(N$^{\alpha,\epsilon}$-di-Boc-lysyloxy)succinimide (3 eq) in DMF was added to peptide 7 (1 eq, 0.006 mmol) followed by NMM (5 eq). After 18 hours the reaction was complete and the solvent was removed under reduced pressure. The peptide residue was treated with TFA containing 2.5% TIS and 2.5% water for 15 min giving Cys2-6; c[CH$_2$CO-Lys(N-Lys)-Cys-Arg-Gly-Asp-Cys-Phe-Cys]-Gly-Lys(Glut-cPn216)-NH$_2$ 8 which was isolated by precipitation and lyophilized as described above.

N-(–5-Sulfo-naphthalen-2-yl)-succinamic acid 3 (10 eq) was activated by HATU (10 eq) in DMF containing NMM (30 eq). After 30 min the mixture was added to a solution of peptide 8 (1 eq) in DMF and the reaction was allowed to proceed for 24 hours. The mixture was worked up as described above and the lyophilized peptide product was purified by preparative RP-HPLC. The column (Phenomenex Luna C18 10μ, 10×250 mm) was eluted at 5 ml/min with a gradient of 10 to 30% ACN in 0.1% aq TFA over 40 min. The desired peak fractions were pooled and lyophilized affording 2 mg of pure peptide 9. Analytical RP-HPLC: $t_R$=17.4 min, (Phenomenex Luna 5μ, 4.6×250 mm, 5-30% ACN in 0.1% aq TFA over 20 min at 1 ml/min, λ=214 nm). MALDI-TOF MS: [M+H]$^+$ of product expected at 2330.95 m/z, found at 2330.27 m/z.

$^{99m}$Tc-Labelling of Peptide 9

Peptide 9 was labelled with $^{99m}$Tc under the conditions described for labelling of peptide 4 in Example 1.

Example 3

Cys2-6; c[CH$_2$CO-Lys(Cy5.5)-Cys-Arg-Gly-Asp-Cys-Phe-Cys]-Gly-Lys(Glut-cPn216)-NH$_2$ 10 its $^{99m}$Tc chelate (10a)

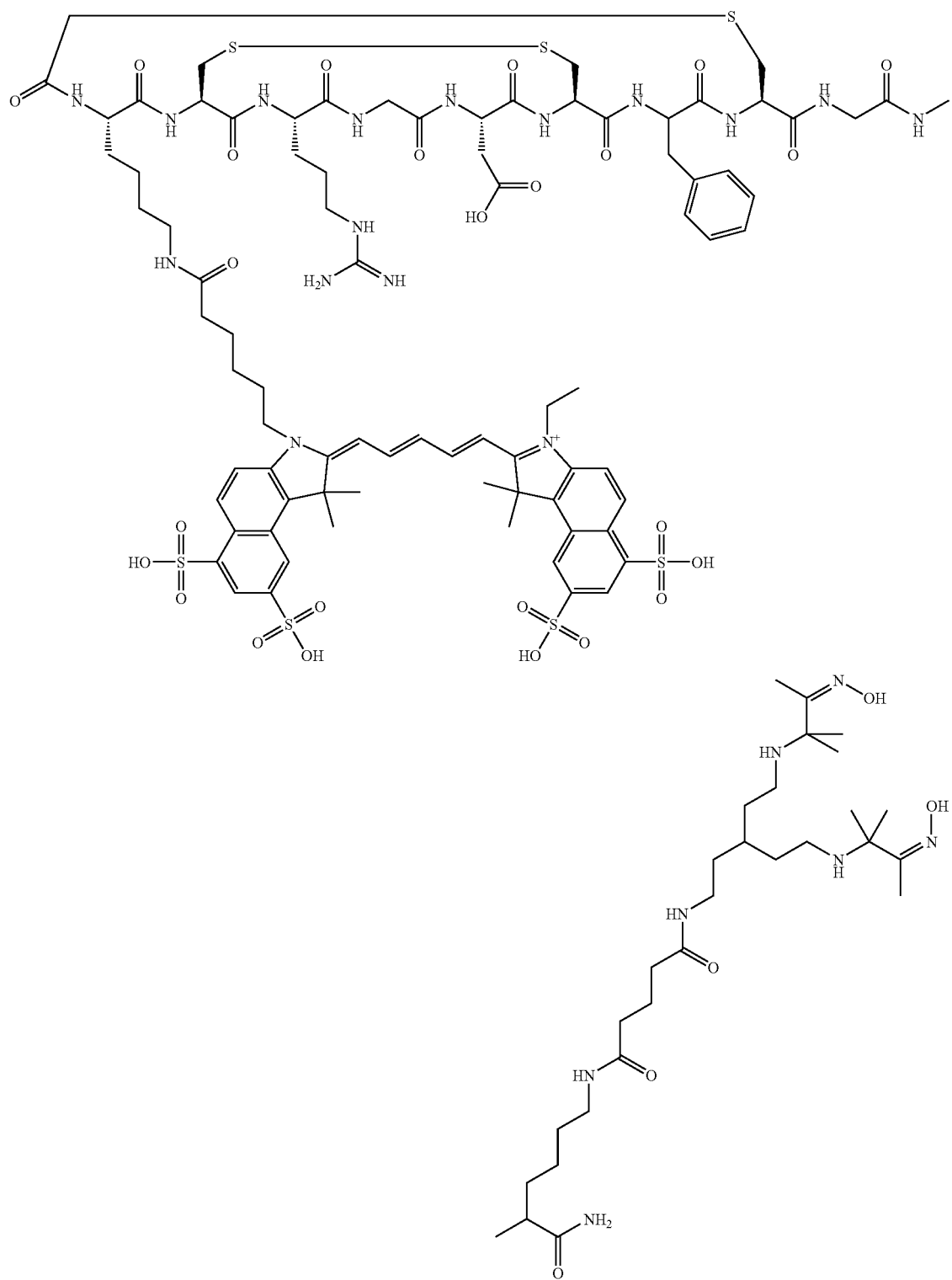

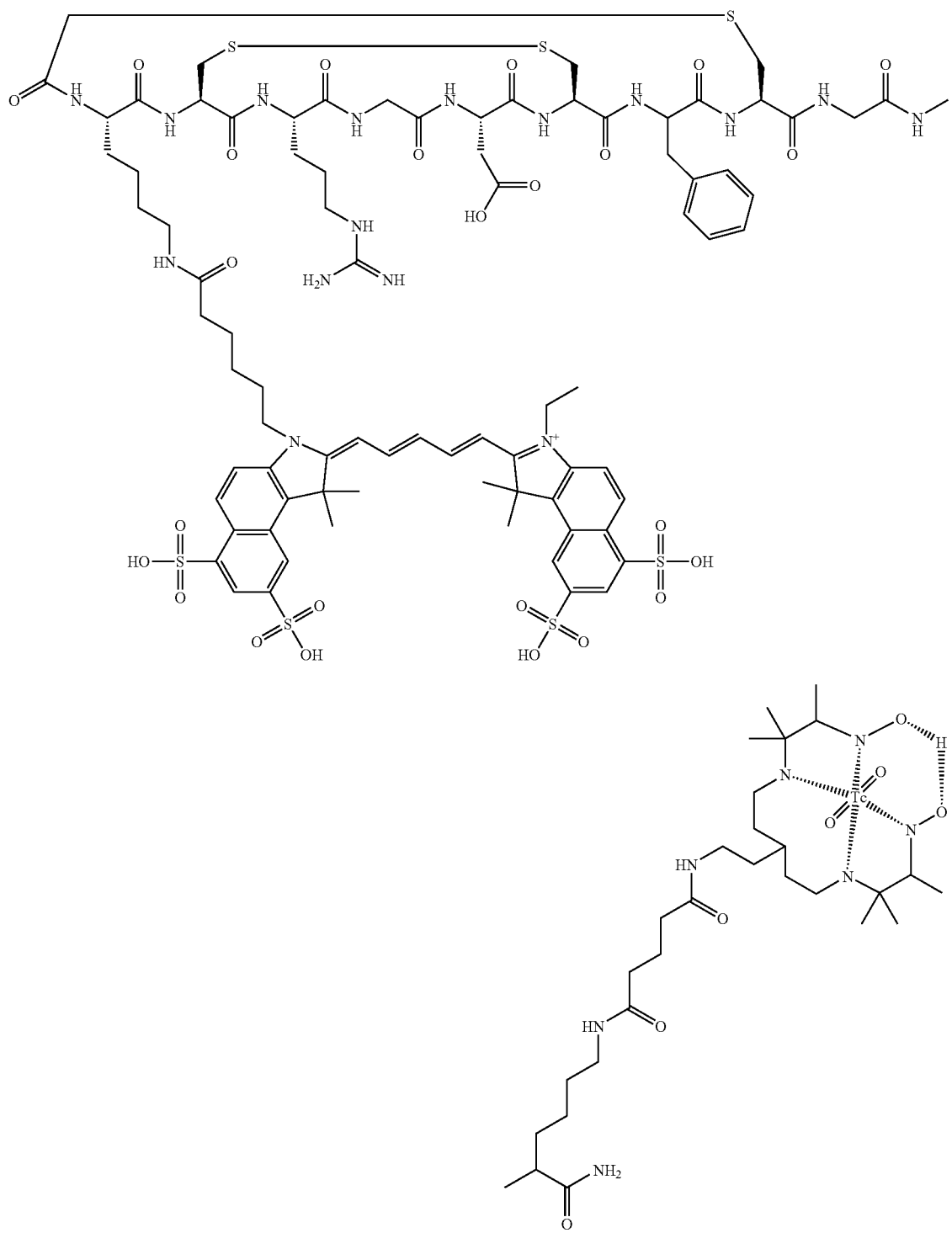

10a

Coupling of Cy5.5 to Peptide 7

Cy5.5-N-hydroxysuccinimide ester (2 eq) was dissolved in NMP and the solution was added to peptide 7 (1 eq. 0.005 mmol) followed by NMM (5 eq). The reaction was let proceed in the dark for two days. The reaction mixture was then concentrated by rotary evaporation at 45 degrees and then diluted with 0.1% aq. TFA and purified by preparative RP-HPLC. The column (Phenomenex Luna C18 10μ, 22×250 mm) was eluted at 10 ml/min with a gradient of 15 to 30% ACN in 0.1% aq TFA over 60 min. The desired peak fractions were pooled and lyophilized to afford 3.2 mg of pure peptide 10. Analytical RP-HPLC: $t_R$=20.9 min, (Phenomenex Luna 5μ, 4.6×250 mm, 15-30% ACN in 0.1% aq TFA over 20 min at 1 ml/min, λ=214 nm). Electrospray MS: $[M+H]^{2+}$ of product expected at 1245.97 m/z, found at 1246.1 m/z.
$^{99m}$Tc-Labelling of Peptide 10
Peptide 10 was labelled with $^{99m}$Tc under the conditions described for labelling of peptide 4 in Example 1.
Example 4
Cys2-6; c[CH$_2$CO-Lys(8-thiouryl-pyrene-1,3,6-trisulfonic acid)-Cys-Arg-Gly-Asp-Cys-Phe-Cys]-Gly-BAEG-Glut-cPn216 14 its $^{99m}$Tc chelate (14a)
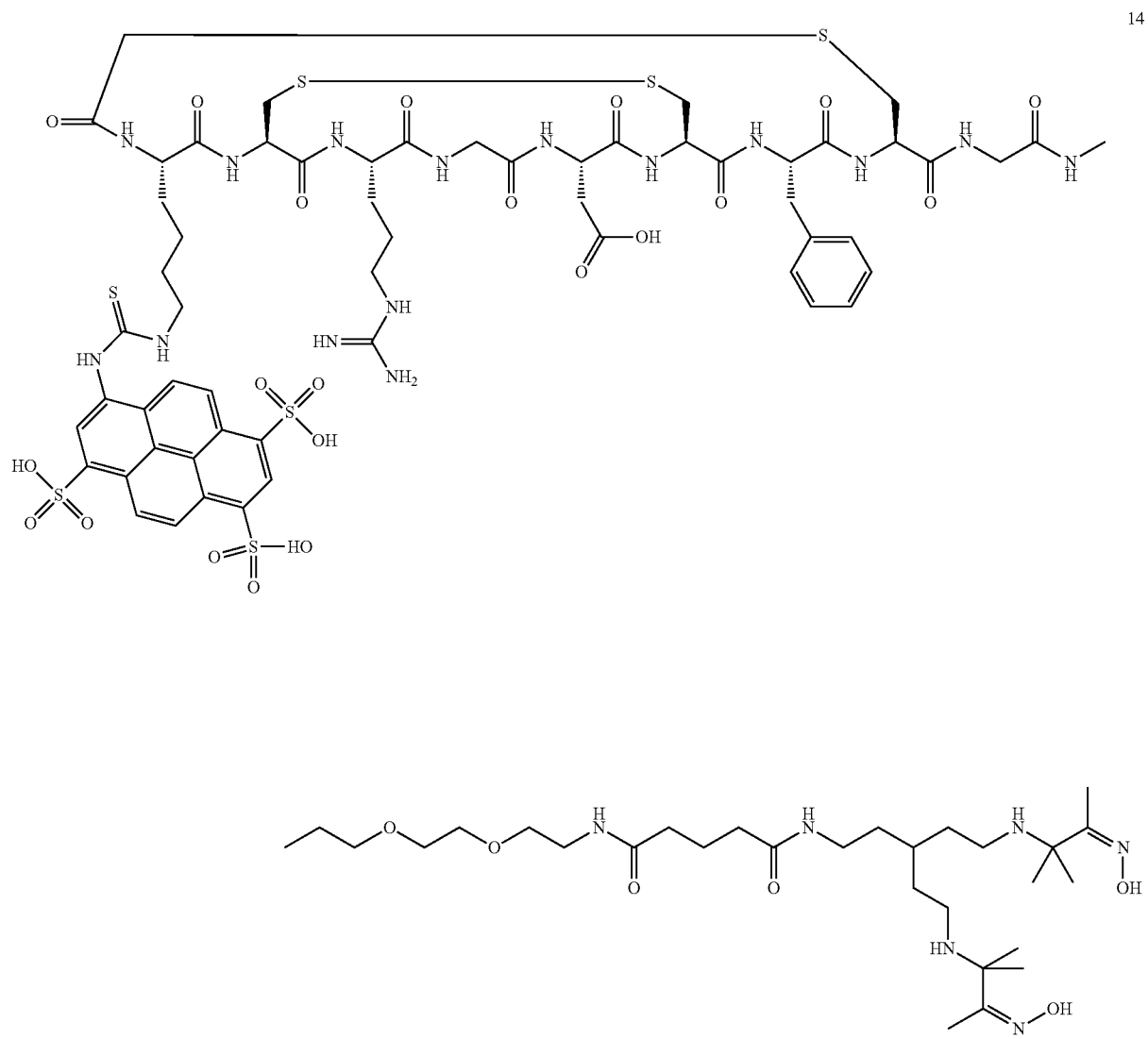

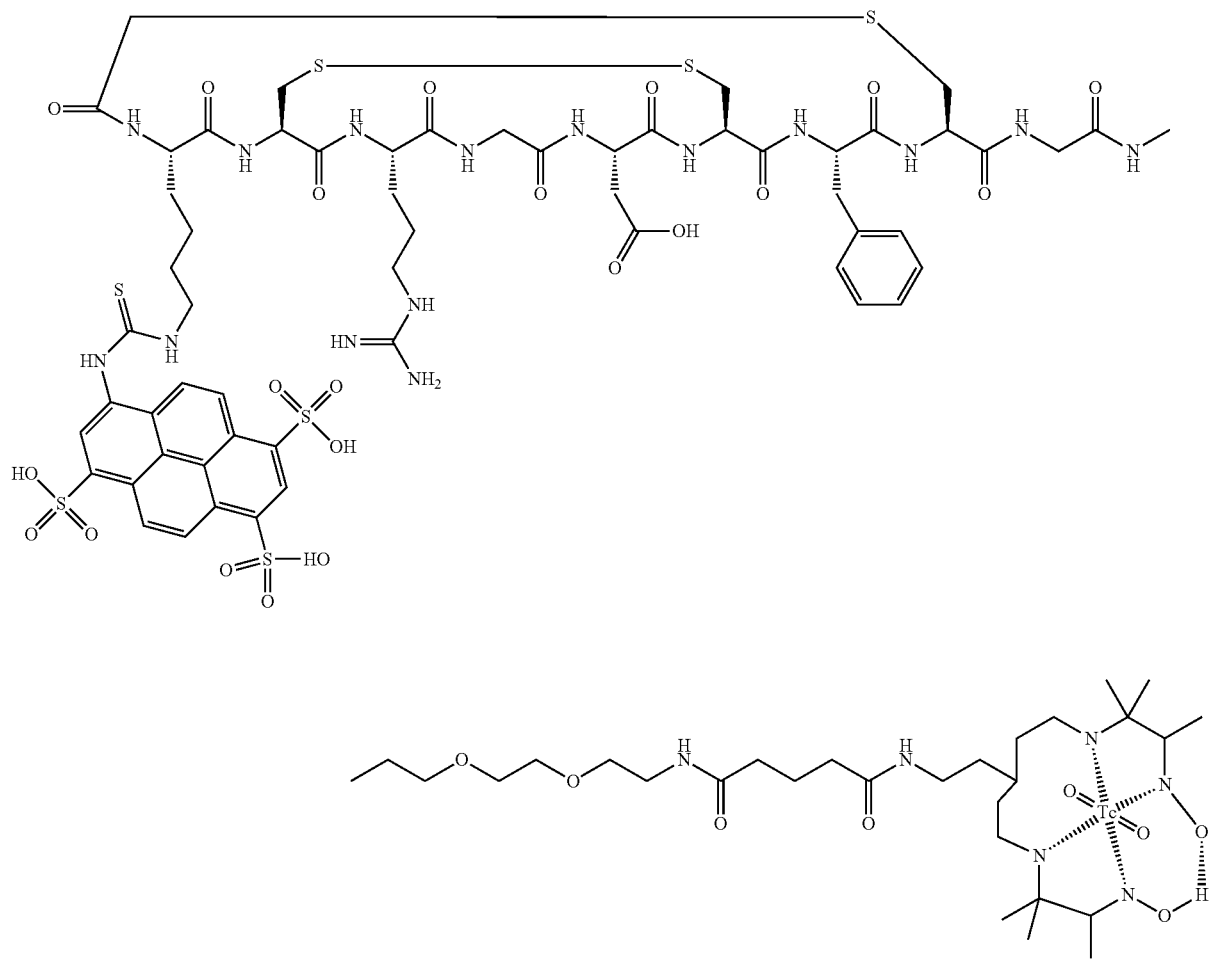

14a

Synthesis of Cys2-6, c[CH₂CO-Lys-Cys-Arc-Gly-Asp-CysPhe-Cys]-Gly-BAEG-Glut-cPN216 13

The peptidyl resin corresponding to the above sequence was assembled on a O-Bis-(aminoethyl)ethylene glycol (BAEG) trityl resin (0.44 mmol/g; from NovaBiochem) in a similar fashion to the peptidyl resin in Example 1. The N$^\epsilon$-Lys$^1$ protecting group used was 1-(4,4-demethyl-2,6-dioxo-cyclohex-1-ylidede)ethyl (Dde). The assembled peptidyl resin was then transferred to a manual nitrogen bubbler apparatus, the N-terminus was Fmoc-deprotected and then chloroacetylated using a 10-fold molar excess of the symmetric anhydride in DMF, formed by reacting chloroacetic acid (20 eq) with DIC (10 eq) in DCM. Cleavage of the partially protected peptide from the resin was effected by treating the peptidyl resin with TFA containing 2.5% TIS and 2.5% water for 2 hours. The reaction mixture was worked up and the peptide ClCH₂CO-Lys(Dde)-Cys(tBu)-Arg-Gly-Asp-Cys(tBu)-Phe-Cys-Gly-DEG-NH₂ 11 was isolated from ether and lyophilized as described above in Example 1.

The linear peptide 11 (30 mg) was cyclized by thioether-bridge formation as described in Example 1 and the crude product was purified by preparative RP-HPLC. The C-18 column (Vydac 218TP1022, 10μ, 22×250 mm) was eluted at 10 ml/min with a gradient of 25 to 40% ACN in 0.1% aq TFA over 60 min. The desired peak fractions were pooled and lyophilized to afford 15 mg of purified peptide c[CH₂CO-Lys(Dde)-Cys(tBu)-Arg-Gly-Asp-Cys(tBu)-Phe-Cys]-Gly-DEG-NH₂ 12. Analytical RP-HPLC: $t_R$=19.2 min, (Phenomenex Luna 5μ, 4.6×250 mm, 25-40% ACN in 0.1% aq TFA over 20 min at 1 ml/min, λ=214 nm). Electrospray MS: [M+H]$^+$ of product expected at 1434 m/z, found at 1434.6 m/z.

Peptide 12 (1 eq, 15 mg) was dissolved in DMF and cPN216-glutaryl-tetrafluorothio-phenyl ester (2 eq) was added followed by NMM (3 eq) and the mixture was stirred over night. The Dde-group at N$^\epsilon$-Lys$^1$ was then removed by adding enough hydrazine to the reaction mixture to give a 2% solution. After 30 min the solvent was removed under reduced pressure and the product was isolated by precipitation and lyophilization as described above. Final tBu-deprotection and disulfide formation of the peptide was done as described in Example 1. The fully cyclized peptide 13 yielded 18 mg.

Conjugation of 8-isothiocyanatopyrene-1,3,6-trisulfonic acid to peptide 13

Peptide 13 (1 eq, 5 mg) was dissolved in DMF and the pH was adjusted to 8 by adding NMM in small aliquots. 8-isothiocyanatopyrene-1,3,6-trisulfonic acid trisodium salt (5 eq) in DMF was then added, and the reaction mixture was stirred over night. The reaction was monitored by RP-HPLC and MS analysis, and the product purified by preparative RP-HPLC. The column (Phenomenex Luna C18 10μ, 22×250 mm) was eluted at 10 ml/min with a gradient of 5 to 60% ACN in 0.1% aq TFA over 60 min. The desired peak fractions were pooled and lyophilized affording 0.8 mg of pure peptide 14. Analytical RP-HPLC: $t_R$=2.04 min (broad peak), (Phenomenex Luna 3μ, 4.6×5 mm, 10-80% ACN in 0.1% aq TFA over 10 min at 2 ml/min, λ=214 nm). Electrospray MS: $[M+H]^{2+}$ of product expected at 1047.8 m/z, found at 1048.2 m/z.

$^{99m}$Tc-Labelling of Peptide 14

Peptide 14 was labelled with $^{99m}$Tc under the conditions described for labelling of peptide 4 in Example 1.

The invention claimed is:

1. A contrast agent of the general formula (I):

Z₁-L-V-Z₂ (I)

wherein
$Z_1$ is a SPECT or PET reporter moiety;
$Z_2$ is an optical imaging reporter moiety;
L comprises one or more dicarboxylic acid units, ethyleneglycol units or a monodisperse PEG-like structure of 17-amino-5-oxo-6-aza-3,9,12,15-tetraoxaheptadecanoic acid of formula (V)

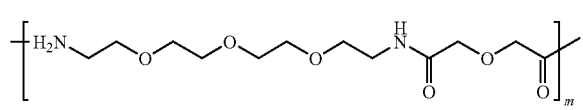

(V)

wherein m equals an integer from 1 to 10 and where the C-terminal unit is an amide moiety; and,
V is a moiety of formula (VI)

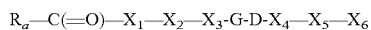

$R_a$—C(=O)—X₁—X₂—X₃-G-D-X₄—X₅—X₆ (VI)

comprising two cyclising bridges,
wherein,
$X_1$ represents a covalent bond or 1, 2, 3, 4 or 5 amino acid residues;
$X_2$ and $X_4$ represent independently amino acids residues that forms a cyclising bridge,
$X_3$ represents arginine, or N-methylarginine;
$X_5$ represents a tyrosine, a phenylalanine, a 3-iodo-tyrosine or a naphthylalanine residue;
$X_6$ represents an amino acid residue that forms a cyclising bridge;
$R_a$ represents the moieties —(CH₂)$_n$— or —(CH₂)$_n$—C₆H₄— that forms a bridge to either of $X_2$, $X_4$ or $X_6$; and
n represents a positive integer from 1 to 10.

2. A contrast agent as claimed in claim 1 wherein $X_1$ represents 1, 2, 3, 4 or 5 amino acid residues wherein at least one of the amino acid residues possesses a functional sidechain comprising an acid or an amine.

3. A contrast agent as claimed in claim 1 wherein $X_2$ and $X_4$ independently represent cysteine or homocysteine residues forming disulphide or thioether bonds, or amino acid residues that forms a cyclising bridge selected from aspartic acid and lysine.

4. A contrast agent as claimed in claim 1 wherein $X_2$ and $X_4$ independently represent residues of cysteine or homocysteine.

5. A contrast agent as claimed in claim 1 wherein $X_5$ represents a tyrosine, a phenylalanine, a 3-iodo-tyrosine or a naphthylalanine residue.

6. A contrast agent as claimed in claim 1 wherein $X_6$ represents an amino-acid residue comprising a thiol.

7. A contrast agent as claimed in claim 1 wherein $X_6$ represents a cysteine or a homocysteine residue.

8. A contrast agent as claimed in claim 1 wherein L represents a peptide comprising 1-10 amino acid residues.

9. A contrast agent as claimed in claim 1 wherein L represents glycine, lysine, aspartic acid or serine residues.

10. A contrast agent as claimed in claim 1 wherein L comprises one or more diclycolyl, glycolyl or succinyl units or combinations thereof.

11. A contrast agent as claimed in claim 1 wherein L represents said monodisperse PEG-like structure of formula (V)

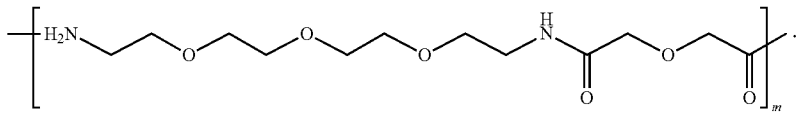

12. A contrast agent as claimed in claim 1 wherein $Z_1$ comprises a non-metal radionuclide covalently linked to L.

13. A contrast agent as claimed in claim 12 wherein $Z_1$ comprises $^{11}$C, $^{18}$F, $^{123}$I, $^{125}$I or $^{131}$I.

14. A contrast agent as claimed in claim 1 wherein $Z_1$ represents a reporter moiety of the formula $Y_1M$ where M is a metal radionuclide and $Y_1$ is a chelating agent that binds L and carries M.

15. A contrast agent as claimed in claim 14 wherein $Y_1$ is a chelating agent of the formula (II)

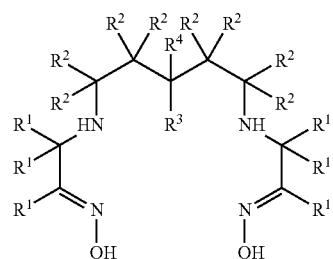

(II)

wherein each $R^1$, $R^2$, $R^3$ and $R^4$ independently represents H, $C_{1-10}$ alkyl, $C_{3-10}$ alkylaryl, $C_{2-10}$ alkoxyalkyl, hydroxyalkyl, $C_{1-10}$ alkylamine, $C_{1-10}$ fluoroalkyl, or 2 or more $R^1$, $R^2$, $R^3$ or $R^4$ groups, together with the atoms to which they are attached form a carbocyclic, heterocyclic, saturated or unsaturated ring.

16. A contrast agent according to claim 15 where the chelating agent is of formula (III)

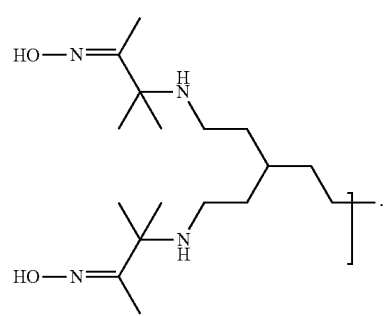

(III)

17. A contrast agent as claimed in claim 16 wherein $Z_2$ is a cyanine dye comprising 2 or more sulfonic acid moieties.

18. A contrast agent as claimed in claim 14 wherein the moiety M is $^{99m}$Tc.

19. A radiopharmaceutical composition comprising an effective amount of a contrast agent of general Formula I as defined in claim 1 or a salt thereof, together with one or more pharmaceutically acceptable adjuvants, excipients or diluents for use in enhancing image contrast in in vivo imaging.

20. A method of generating enhanced images of a human or animal body administered with a contrast agent composition comprising a contrast agent of Formula I as defined in claim 1, which method comprises generating an image of at least part of said body.

21. A kit for the preparation of a radiopharmaceutical composition comprising the contrast agent of Formula I as defined in claim 14, said kit comprising a ligand-chelate conjugate and a reducing agent.

22. A kit for the preparation of a radiopharmaceutical composition of formula I:

$$Z_1\text{-L-V-}Z_2 \qquad (I)$$

wherein
$Z_1$ is a SPECT or PET reporter moiety;
$Z_2$ is an optical imaging reporter moiety;
L comprises one or more dicarboxylic acid units, ethyleneglycol units or a monodisperse PEG-like structure of 17-amino-5-oxo-6-aza-3,9,12,15-tetraoxaheptadecanoic acid of formula (V)

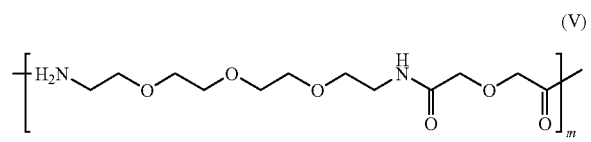

(V)

wherein m equals an integer from 1 to 10 and where the C-terminal unit is an amide moiety; and,
V is a moiety of formula (VI)

$$R_a\text{—C(=O)—}X_1\text{—}X_2\text{—}X_3\text{-G-D-}X_4\text{—}X_5\text{—}X_6 \qquad (VI)$$

comprising two cyclising bridges,
wherein,
$X_1$ represents a covalent bond or 1, 2, 3, 4 or 5 amino acid residues;
$X_2$ and $X_4$ represent independently amino acids residues that forms a cyclising bridge,
$X_3$ represents arginine, or N-methylarginine;
$X_5$ represents a tyrosine, a phenylalanine, a 3-iodo-tyrosine or a naphthylalanine residue;
$X_6$ represents an amino acid residue that forms a cyclising bridge;
$R_a$ represents the moieties —$(CH_2)_n$— or —$(CH_2)_n$—$C_6H_4$— that forms a bridge to either of $X_2$, $X_4$ or $X_6$; and
n represents a positive integer from 1 to 10;
wherein the kit comprises a ligand-chelate conjugate and a reducing agent.

23. The kit of claim 22 where the reducing agent is a stannous salt.

24. The kit of claim 22 additionally comprising one or more stabilisers, antioxidants, bulking agents for lyophilisation and solubilisers.

25. The contrast agent of claim 2, wherein said amino acid residue possessing a functional side-chain is aspartic acid, glutamic acid, diaminobutyric acid or diaminopropionic acid.

26. The contrast agent of claim 2, wherein said amino acid residue possessing a functional side-chain is lysine or ornithine.

* * * * *